US008551074B2

(12) United States Patent
Hoffman et al.

(10) Patent No.: US 8,551,074 B2
(45) Date of Patent: Oct. 8, 2013

(54) CONNECTOR SYSTEM HAVING A COMPRESSIBLE SEALING ELEMENT AND A FLARED FLUID PATH ELEMENT

(75) Inventors: Raymond C. Hoffman, Gibsonia, PA (US); Edward J. Rhinehart, Monroeville, PA (US); Kevin P. Cowan, Allison Park, PA (US); Barry L. Tucker, Verona, PA (US)

(73) Assignee: Bayer Pharma AG (DE)

( * ) Notice: Subject to any disclaimer, the term of this patent is extended or adjusted under 35 U.S.C. 154(b) by 478 days.

(21) Appl. No.: 12/206,123

(22) Filed: Sep. 8, 2008

(65) Prior Publication Data

US 2010/0063481 A1 Mar. 11, 2010

(51) Int. Cl.
*A61M 25/18* (2006.01)

(52) U.S. Cl.
USPC .......................... 604/535; 604/264; 604/523

(58) Field of Classification Search
USPC .......... 604/523, 529, 535, 533, 536, 538, 539
See application file for complete search history.

(56) References Cited

U.S. PATENT DOCUMENTS

| | | | |
|---|---|---|---|
| 5,004,457 A | 4/1991 | Wyatt et al. | |
| 5,383,454 A | 1/1995 | Bucholz | |
| 5,622,170 A | 4/1997 | Schulz | |
| 5,795,340 A * | 8/1998 | Lang | 604/533 |
| 5,871,445 A | 2/1999 | Bucholz | |
| 5,891,034 A | 4/1999 | Bucholz | |
| 5,920,395 A | 7/1999 | Schulz | |
| 6,236,875 B1 | 5/2001 | Bucholz et al. | |
| 6,299,591 B1 * | 10/2001 | Banko | 604/22 |
| 6,347,240 B1 | 2/2002 | Foley et al. | |
| 6,463,319 B1 | 10/2002 | Bucholz | |
| 6,503,242 B1 | 1/2003 | Elsberry | |
| 6,565,551 B1 * | 5/2003 | Jones et al. | 604/507 |
| 6,641,574 B2 * | 11/2003 | Badia Segura | 604/533 |
| 6,678,545 B2 | 1/2004 | Bucholz | |
| 6,709,427 B1 | 3/2004 | Nash et al. | |
| 6,955,660 B2 * | 10/2005 | Fisher | 604/240 |
| 7,072,704 B2 | 7/2006 | Bucholz | |
| 7,137,969 B1 | 11/2006 | Mendez | |
| 7,666,177 B2 | 2/2010 | Guest et al. | |

(Continued)

FOREIGN PATENT DOCUMENTS

| | | |
|---|---|---|
| WO | 9206645 | 4/1992 |
| WO | 9423647 | 10/1994 |

(Continued)

*Primary Examiner* — Kevin C Sirmons
*Assistant Examiner* — Brandy S Lee
(74) *Attorney, Agent, or Firm* — David Schramm (57) ABSTRACT

Systems for connecting a conduit to an injection needle may include a sealing element positioned on a distal end of the conduit, a first cooperating connector positioned around the length of conduit proximal to the sealing element and a second cooperating connector. The first cooperating connector includes a first cooperating connection mechanism and the second cooperating connector includes a second cooperating connection mechanism having a passage therein. The first cooperating connection mechanism and the second cooperating connection mechanism are adapted to form a connection between the first cooperating connector and the second cooperating connector. The connection causes the compression of the sealing element. The injection needle has a lumen with a diameter flared outward to a larger diameter at a proximal end. The second cooperating connector has a mounting hole connected to the passage and a sleeve around the injection needle so that the sleeve and the injection needle are received within the mounting hole.

18 Claims, 5 Drawing Sheets

(56) References Cited

U.S. PATENT DOCUMENTS

| | | | |
|---|---|---|---|
| 2003/0032940 A1* | 2/2003 | Doyle | 604/533 |
| 2004/0030250 A1 | 2/2004 | Stewart | |
| 2004/0172006 A1* | 9/2004 | Bonaldo | 604/523 |
| 2004/0191225 A1 | 9/2004 | Dinsmore et al. | |
| 2004/0210196 A1 | 10/2004 | Bush, Jr. et al. | |
| 2005/0085790 A1 | 4/2005 | Guest et al. | |
| 2005/0225082 A1 | 10/2005 | Dalle et al. | |
| 2007/0106208 A1 | 5/2007 | Uber, III et al. | |
| 2008/0086111 A1 | 4/2008 | Cowan et al. | |
| 2008/0294096 A1 | 11/2008 | Uber, III et al. | |
| 2009/0012497 A1 | 1/2009 | Uber, III et al. | |

FOREIGN PATENT DOCUMENTS

| | | |
|---|---|---|
| WO | 9424933 | 10/1994 |
| WO | 9521643 | 8/1995 |
| WO | 9611624 | 4/1996 |
| WO | WO2007053779 | 5/2007 |
| WO | WO2007056247 | 5/2007 |
| WO | 2007064937 | 7/2007 |
| WO | 2007065013 | 7/2007 |

* cited by examiner

CONNECTOR SYSTEM HAVING A COMPRESSIBLE SEALING ELEMENT AND A FLARED FLUID PATH ELEMENT

BACKGROUND OF THE INVENTION

The present invention relates to flow path assemblies and, particularly, to flow path assemblies for use in a fluid path for delivery of medical fluids.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosures of all references cited herein are incorporated by reference.

The treatment of disease by the injection of living cells into a body is expanding rapidly. There are many types of cells being used to treat an equally diverse set of diseases, and both types of cells and disease conditions are expanding rapidly. Xenogeneic cell therapies involve implantation of cells from one species into another. Allogeneic cell therapies involve implantation from one individual of a species into another individual of the same species. Autologous cell therapies involve implantation of cells from one individual into the same individual. Cell components can also have a beneficial effect on the body in selected instances. Any of the above therapies are examples of approaches that can be delivered with the systems and methods of this invention.

Figure 1A:
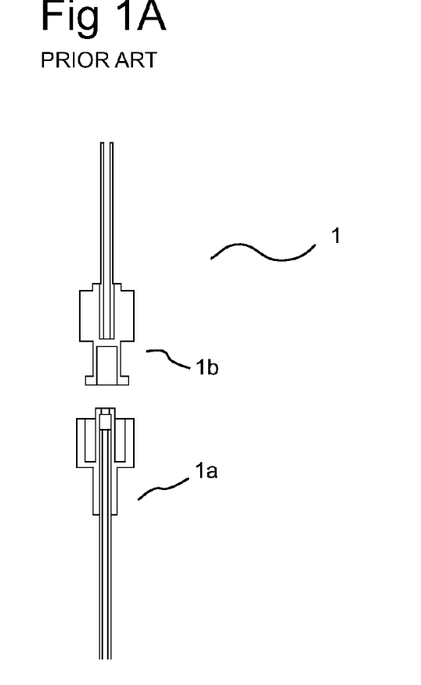
FIG. 1A illustrates a standard luer-type connector in a disconnected state.
Figure 1B:
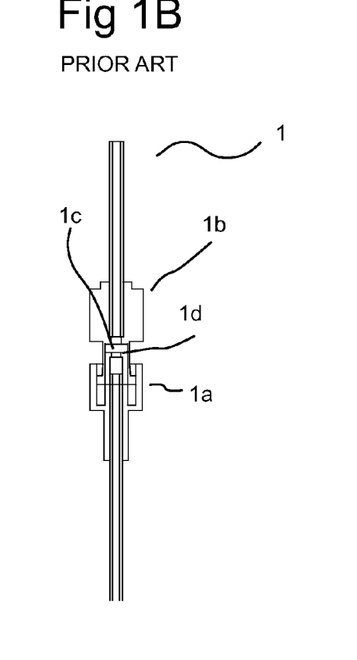
FIG. 1B illustrates the standard luer-type connector of FIG. 1A in a connected state.
Figure 1C:
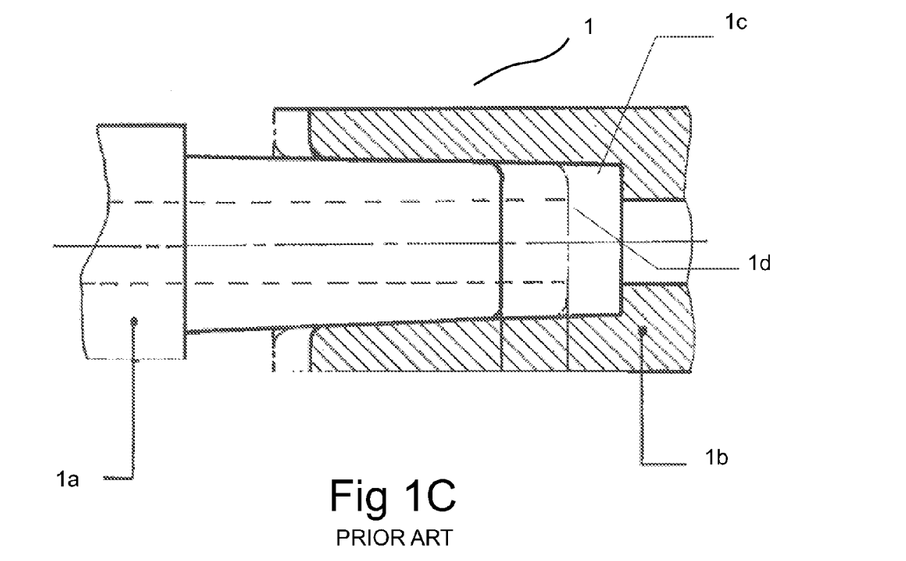
FIG. 1C illustrates an enlarged cross-sectional view of the connected luer-type connector of FIG. 1A, illustrating sharp transitions in the flow path and areas of potential lost volume.

Deleterious effects of flow of cells through fluid paths are not well addressed in many current fluid paths. For example, standard luer connectors are used almost universally in the current medical practice, including in fluid paths for cell delivery. An example of a standard luer connector 1 is shown in FIGS. 1A through 1C. FIG. 1C is taken from the standard ISO 594-1-1986, FIG. 2. As the tapered sections of the male 1a and female 1b connectors mate, a dead space is created as indicated by 1c. In addition, the sharp transition in the fluid path at the end of the male luer, as indicated at 1d, can create turbulence and increase shear stress in the fluid and on the cells, resulting in cell damage or even death. Moreover, similar problems exist in commonly used fluid path elements other than luer-type connectors.

It is desirable to develop improved fluid path assemblies that reduce or eliminate the above and/or other problems associated with currently available fluid path assemblies.

SUMMARY OF THE INVENTION

In one aspect, the present invention provides a system for connecting a conduit to a fluid path element, including: a length of conduit, a compressible sealing element positioned on a distal end of the length of conduit to be attached to the fluid path element, a first cooperating connector positioned around the length of conduit proximal to the sealing element and a second cooperating connector. The first cooperating connector includes a first cooperating connection mechanism and the second cooperating connector includes a second cooperating connection mechanism. The first cooperating connection mechanism and the second cooperating connection mechanism are adapted to form a connection between the first cooperating connector and the second cooperating connector. The connection causes the compression of the sealing element. The second cooperating connector further includes a passage therein in fluid connection with a connection for the fluid path element. The compressible sealing element can, for example, include or be formed wholly of an elastomeric material.

In several embodiments, at least one of the first cooperating connection mechanism and the second cooperating connection mechanism includes threading.

The fluid path element can, for example, be an injection needle.

In a number of embodiments, the first cooperating connector is a male luer-type connector including threading and the second cooperating connector is a female luer-type connector.

A distal end of the sealing element can, for example, be shaped to approximately conform to a surface of the second cooperating connector with which the distal end of the sealing element comes into contact. For example, each of the distal end of the sealing element and the surface of the second cooperating connector can be angled to approximately the same angle.

In embodiments in which the flow path element is a needle, the needle can include a lumen therethrough. The diameter of the lumen can, for example, be flared outward (that is, increased in diameter) to a larger diameter at a proximal end of the needle. The inner diameter of the proximal end can be greater than the diameter of the passage of the second cooperating connector. The outer diameter of the proximal end of the needle is also preferably flared outward. The connection of the second cooperating connector can, for example, include a seating having a diameter larger than the outer diameter of the proximal end of the needle. The system can further include a sleeve positioned around the needle having an outer diameter at least equal to the outer diameter of the flared proximal end of the needle. A proximal end of the sleeve can abut the needle along the flared proximal end thereof. The sleeve can be attached to the seating. In several embodiments, the sleeve extends over at least the majority of the length of the needle.

In another aspect, the present invention provides a system for connecting to a fluid path section. The system includes a connector including a connection mechanism to connect the connector to the fluid path section and a passage therethrough. The passage is in fluid connection with a first fluid path element downstream of the connector. The first fluid path element includes a lumen therethrough. The diameter of the lumen is flared outward to a larger diameter at a proximal end of the fluid path element. The proximal end of the first fluid path element can abut a surface of the connector in which the distal end of the fluid path is formed. The inner diameter of the proximal end is greater than the diameter of the passage of the second cooperating connector. The outer diameter of the proximal end of the first fluid path element can also be flared outward.

In several embodiments, the first fluid path element is an injection needle.

The connector can, for example, include a seating having a diameter larger than the outer diameter of the proximal end of the needle. The system can further include a sleeve positioned around the needle which has an outer diameter at least equal to the outer diameter of the proximal end of the needle. A proximal end of the sleeve can abut the needle along the flared proximal end thereof. The sleeve can be attached to the seating. In several embodiments, the sleeve extends over at least the majority of the length of the needle.

The connector can, for example, be a second cooperating connector, and the fluid path can include a first cooperating connector to which the second cooperating connector is connectible. At least one of the first cooperating connection mechanism and the second cooperating connection mechanism can, for example, include threading.

In a number of embodiments, the first cooperating connector is a male luer-type connector including threading and the second cooperating connector is a female luer-type connector.

The fluid path can, for example, include a length of conduit including a compressible sealing element positioned on a distal end of the length of conduit. The first cooperating connector can be positioned around the length of conduit proximal to the sealing element. Connection between the first cooperating connector and the second cooperating connector can cause compression of the sealing element. The compressible sealing element can, for example, include or be formed wholly of an elastomeric material.

The distal end of the sealing element can, for example, be shaped to approximately conform to a surface of the second cooperating connector with which the distal end of the sealing element comes into contact. Each of the distal end of the sealing element and the surface of the second cooperating connector can, for example, be angled to approximately the same angle.

The present invention, along with the attributes and attendant advantages thereof, will best be appreciated and understood in view of the following detailed description taken in conjunction with the accompanying drawings.

DETAILED DESCRIPTION OF THE INVENTION

As used herein and in the appended claims, the singular forms "a," "an", and "the" include plural references unless the content clearly dictates otherwise. Thus, for example, reference to "a sealing element" includes a plurality of such sealing elements and equivalents thereof known to those skilled in the art, and so forth, and reference to "the sealing element" is a reference to one or more such sealing elements and equivalents thereof known to those skilled in the art, and so forth.

In general, any component with which a fluid comes into contact during, for example, a fluid delivery or transport procedure is considered part of the fluid path. In most medical applications for the injection of fluid, tubing sets and other fluid path elements have no specific requirements other than containing system pressure without leaking and compatibility with the injection fluids. However, in certain applications that have more specific requirements including, but not limited to, cell delivery, delivery of ultrasound contrast and delivery of nuclear medicine, numerous currently available fluid path elements (including, for example, tubing sets and connectors for use therewith, such as, for example, luer fittings or connectors) have serious shortfalls.

As described herein, in the case of delivery of cells, there is a sensitivity to shear stresses induced in the cells. Within the fluid path (in the fluid delivery stage or elsewhere—for example, in the cell harvesting, cell storage, cell processing, cell delivery or any intermediate stages) turbulent stresses contribute strongly to mechanical trauma of cells. Conditions that contribute to or promote turbulence, including wall irregularities, abrupt changes in tube dimensions, and disturbed flow upstream of a region of interest, are common in current practice, as illustrated in the luer connector in FIGS. 1A through 1C. Wall irregularities and abrupt or sharp transitions can also result in clogging. In this invention, cell damage (and/or damage to other sensitive fluid components) resulting from hydrodynamic forces during handling and delivery of injection fluid, as well as clogging, are preferably minimized by reducing the occurrence of or eliminating such conditions to, for example, improve therapeutic value. Cumulative and peak shear stresses are preferably reduced or minimized.

Moreover, there is a sensitivity to lost volume (as, for example, relatively small volumes are typically delivered). Further, trapped material left in a connector can present a biohazard. Similarly, in delivery of ultrasound contrast there is a sensitivity to lost volume as small volumes are typically delivered. Moreover, standard or conventional fittings used in the industry have areas where bubbles can collect. Nuclear medicine also uses relatively small volumes. Moreover, any trapped material left in a connector presents a radioactive hazard.

Currently, luer fitting are widely used as connectors in connection with medical tubing sets and other medical components. The design of luer fittings cause the formation of small volumes of fluid that are not in the direct fluid path. That is, there are small volumes in the luer connector wherein material can collect and not be removed by a flush. These common luer fittings are not designed to maintain constant uniform diameter throughout the system.

Figure 2A:
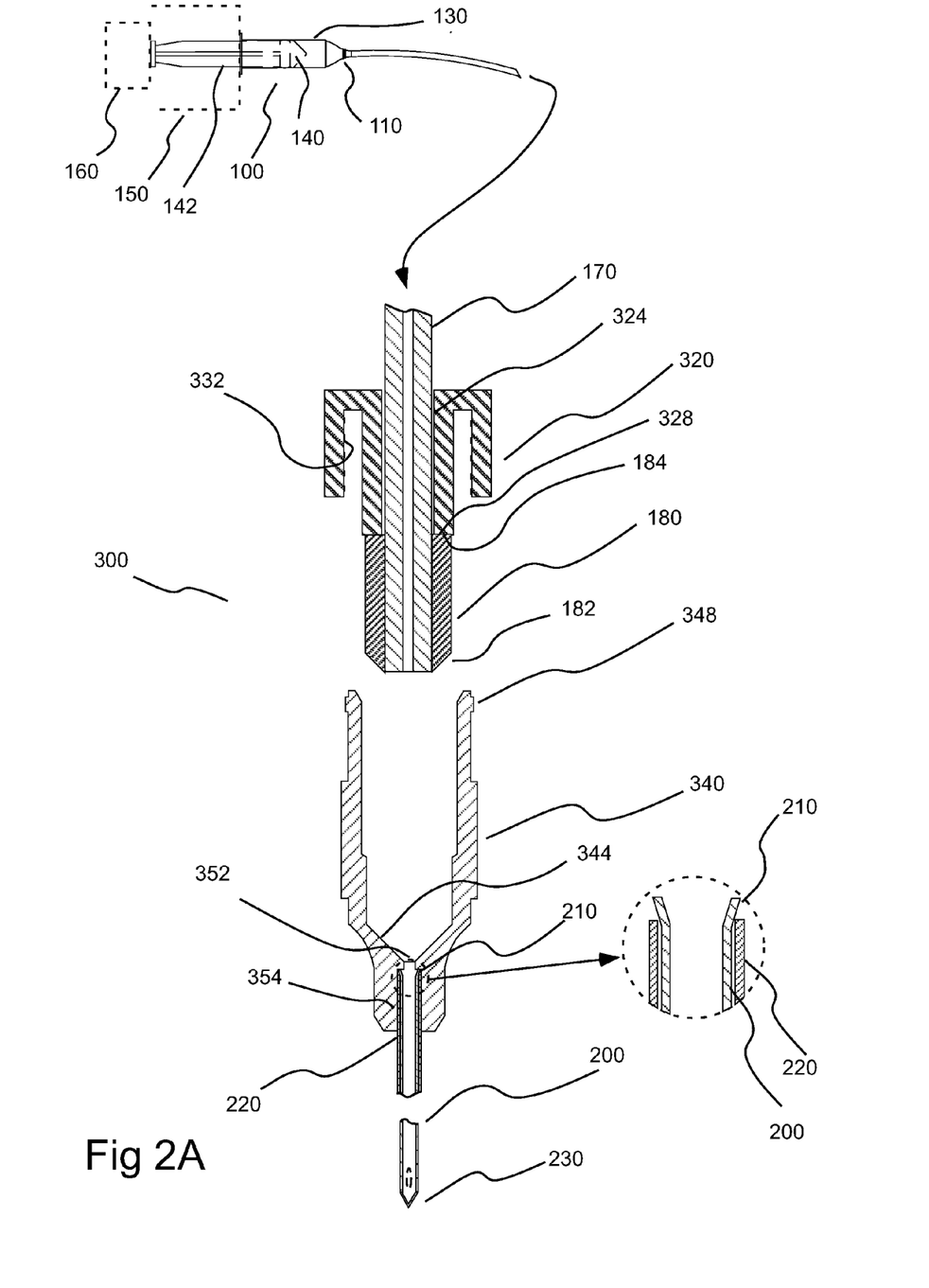
FIG. 2A illustrates a cross-sectional view of a fluid path connector system of the present invention in a disconnected state.
Figure 2B:
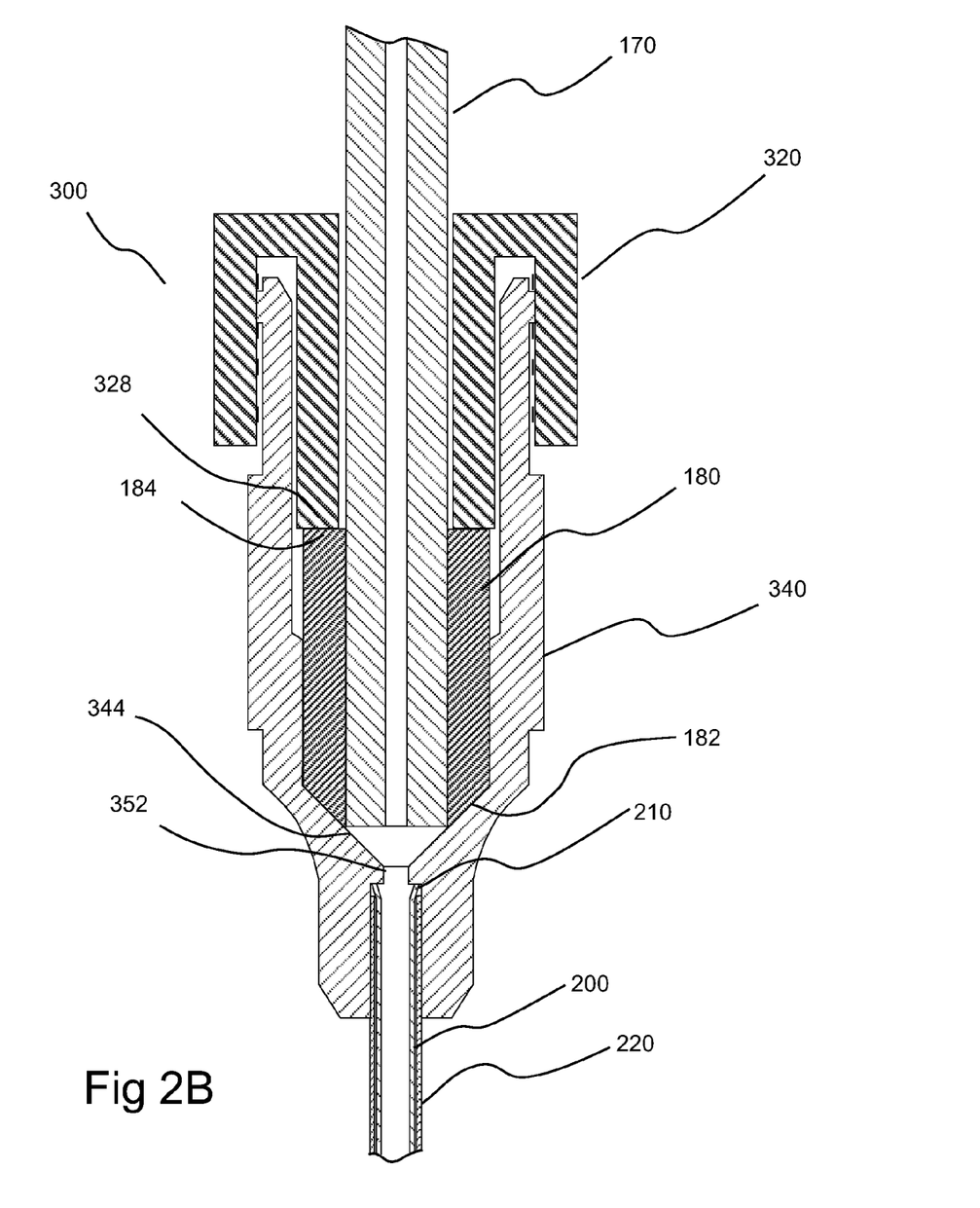
FIG. 2B illustrates a cross-sectional view of a fluid path connector system of the present invention in a connected state.

In, for example, cases where a delivery syringe 100 (for pressurizing a fluid to be delivered) and a patient interface, such as a needle 200 (see FIG. 2), cannot be directly attached, it may be necessary to have a length of tubing or conduit between these two fluid path elements. In several embodiments, devices and systems of the present invention provide for attachment of conduit such as elastomeric tubing to a connector. The connector can, for example, include a male or female luer-type connector to which a patient interface in the form of needle 200 is in fluid connection.

Hydrodynamic forces can, for example, be reduced by providing for gradual transition within and between all fluid path elements. One goal of the devices and systems of the present invention is thus to limit sharp transitions in the fluid path that can damage the cells (and/or other fluid components) being delivered. Eliminating sharp transitions can also assist in preventing clogging, particularly where sharp transitions result in a projecting obstruction in the flow path. Another goal is to reduce residual volume within the system. As described above, such extra volume can provide space for cells and/or other fluid components to collect.

In the embodiment of the present invention illustrated in FIGS. 2A and 2B, syringe 100 is removably connectible to a connector system 300 comprising a first or male cooperating connector 320 and a second or female cooperating connector 340. Needle 200 is in operative and fluid connection with second cooperating connector 340. In several embodiments, first cooperating connector 320 and second cooperating connector 340 were formed from a polymeric material such as vinyl, polyvinyl chloride (PVC), PEBAX® (a polyether block amide available from Arkema, Inc. of Philadelphia, Pa.) etc. or a metallic material such as stainless steel. Conduit 170, such as elastomeric tubing fabricated from vinyl, PVC, PEBAX, C-FLEX® (a silicone-modified styrenic thermoplastic elastomer, available from Consolidated Polymer Technologies, Inc. of Clearwater, Fla.), etc., as known in the medical arts, can be placed in, for example, removable fluid connection with an outlet 110 of syringe 100. As known in the art, syringe 100 includes a barrel 130 and a plunger 140 slidably disposed within barrel 130 to pressurize fluid within barrel 130. Syringe 100 can, for example, be operated manually via a plunger extension 142 as known in the art. As also known in the art, syringe 100 can be placed in operative connection with an injector 150 including a powered drive mechanism 160, which can, for example, cooperate with plunger extension 142 or with plunger 140 to pressurize fluid within syringe barrel 130. Injector systems for delivery of, for example, cells are disclosed, for example, in Published PCT International Patent Application No. WO/2007/053779, the disclosure of which is incorporated herein by reference.

In the illustrated embodiment, conduit 170 has attached to the end thereof opposite the end attached to syringe outlet 110 a compressible sealing element 180. In several embodiments, sealing element 180 included or was formed of an elastomeric material such as vinyl, PVC, PEBAX, C-FLEX, silicone, polyurethane etc. Sealing element 180 can, for example, be generally cylindrical in shape and dimensioned to be concentric with the conduit or tubing 170. In several embodiments, elastomeric sealing element 180 was overmolded onto tubing 170, thereby eliminating the need for an adhesive. Sealing element 180 can alternatively be formed integrally and of the same material as conduit 170.

A distal end of sealing element 180 can, for example, be flush with the distal end of conduit or tubing 170 or extend beyond the distal end of conduit or tubing with a hole aligned with the ID of the tubing. In either case, the base of distal end of sealing element 180 can be shaped, for example, tapered, to generally match the inside surface of the second cooperating connector 340, with which it comes into contact upon connection of first cooperating connector 320 and second cooperating connector 340. Tapered section 182 provides a sealing surface between surface 344 of second cooperating connector 340 and sealing element 180.

Connection of first cooperating connector 320 and second cooperating connector 340 causes compression of sealing element 180 to effect a seal. In the illustrated embodiment, first cooperating connector 320 (a cap or male luer-type cooperating connector) includes a passage 324 through which conduit or tubing 170 passes. A distal end surface 328 of first cooperating connector contacts a proximal end surface or shoulder 184 of sealing element 180 to compress sealing element 180 and to lock it in place within second cooperating connector 340 (a female luer type cooperating connector). As a cooperating engagement member 348 of second cooperating connector 340 engages threading 332 (for example, luer-type threading as known in the arts) of first cooperating connector 320, distal end surface 328 of first cooperating connector contacts surface 184 of sealing element 180, forcing tapered section 182 of sealing element 180 against tapered surface/base 344 of second cooperating connector 340. The inner diameter of second cooperating connector 340 can be made sufficiently large to prevent locking tapers when connector 300 is connected or assembled.

Figure 3:
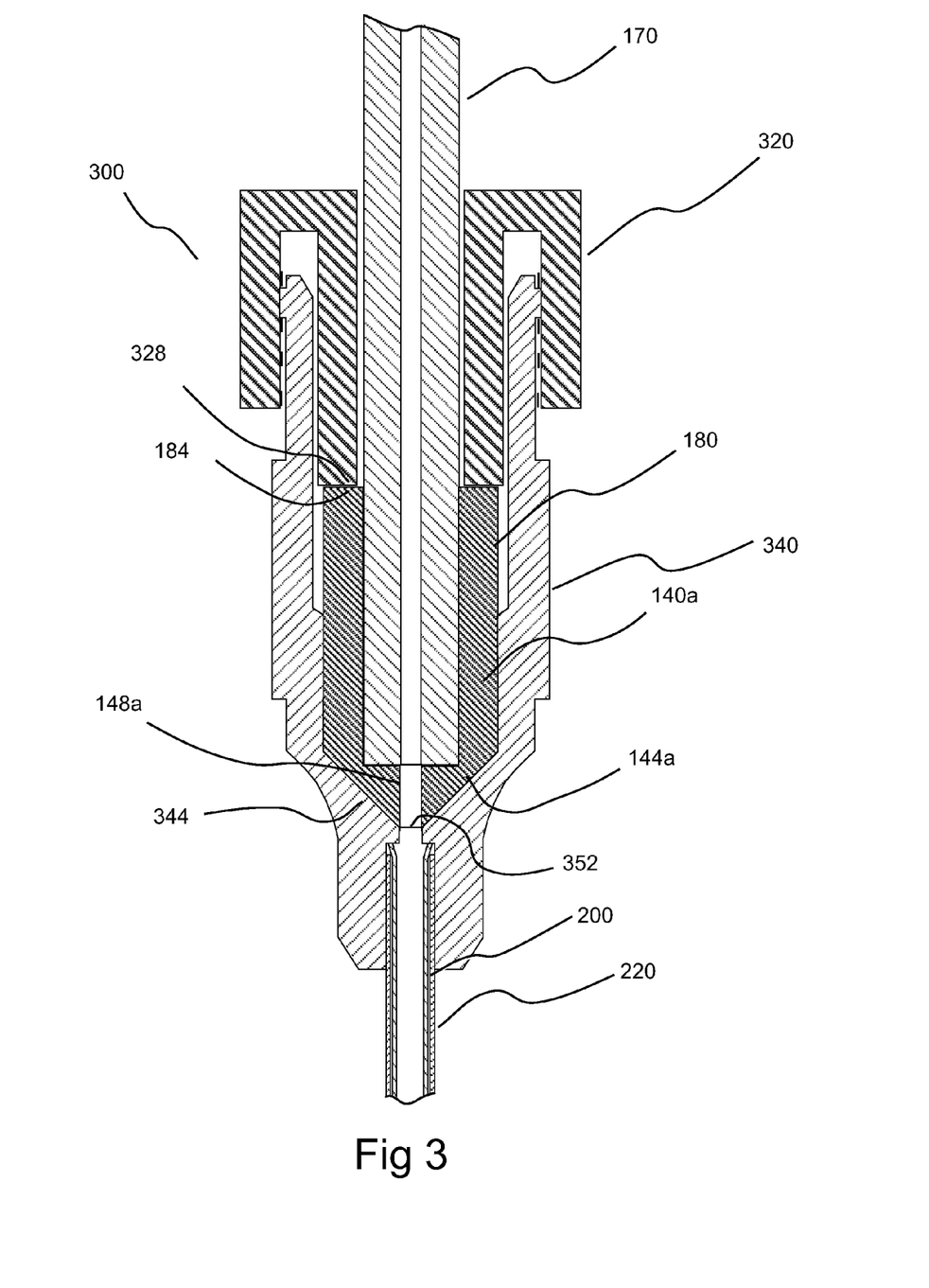
FIG. 3 illustrates another embodiment of a fluid path connector system of the present invention wherein an elastomeric sealing element extends beyond a length of conduit to which the sealing element is attached.

As compared to standard luer-type connectors (as, for example, illustrated in FIGS. 1A through 1C), in the devices and systems of the present invention, the distal end or exit of conduit or tubing 170 is positioned more closely to a flow path opening 352 of second cooperating connector 340, thereby reducing potential lost volume as described in connection with FIGS. 1A through 1C. Alternatively, extending a sealing element 140a beyond the end of conduit or tubing 170 and matching the dimension of a passage 148a within sealing element 140a to passage 352, as illustrated in FIG. 3 can virtually eliminate such potential lost volume.

The interconnection between second cooperating connector 340 and the downstream fluid path element attached thereto (needle 200 in the illustrated embodiment) is also designed to reduce or eliminate sharp flow transitions (which can, for example, damage cells and/or other fluid components being administered). Sharp transitions can, for example, occur between connection of any two fluid path elements or internally within a particular fluid path element.

Figure 4:
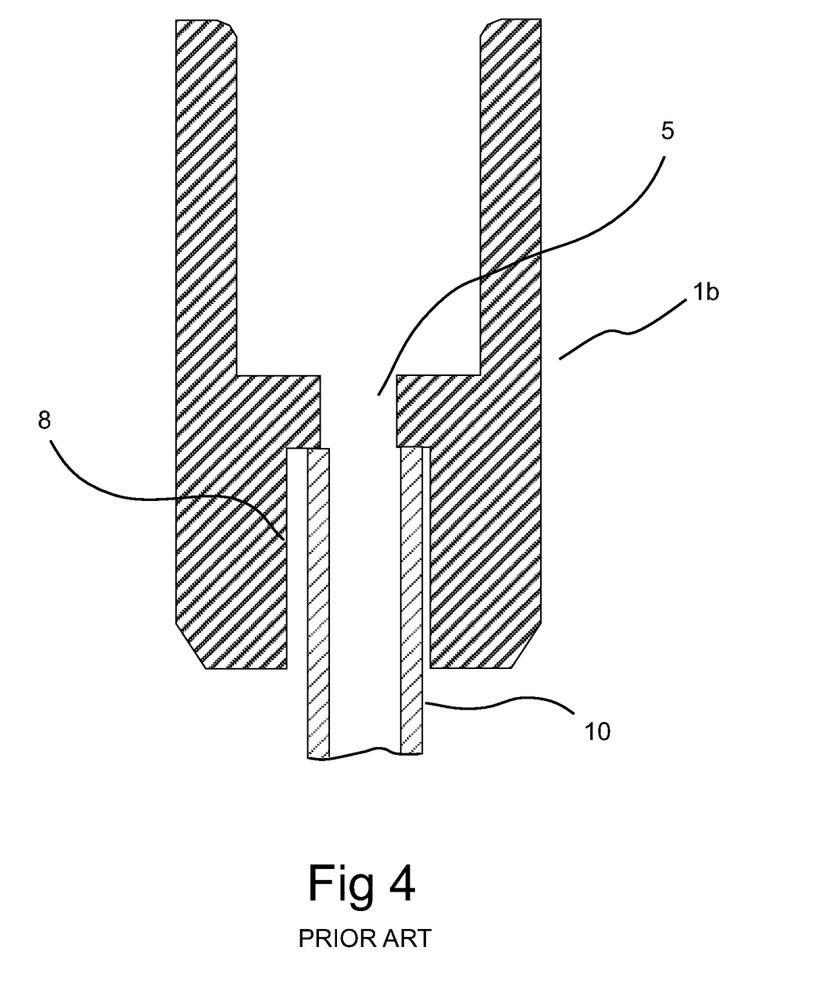
FIG. 4 illustrates an example of needle misalignment and the resultant flow restriction that occurs with current needle assembly procedures in the case of, for example, a female luer-type connector.

Under current practice, the distal end or tip of a female luer-type connector 1b (see FIG. 4) is formed as a solid piece of polymeric or metallic material and is subsequently custom machined to accommodate the fluid path element to be attached thereto, for example, various needle shapes and sizes. Typically, under current practice, a hole 5 is machined through the luer tip matching the inner diameter of needle 10 to be attached. A second hole 8, slightly larger than the outer diameter of needle 10, is then drilled into the front of the luer tip, leaving a small length of original through hole 5. Needle 10 is then inserted into larger hole 8 and welded or soldered into place. As a result of the clearances required to assemble needle 10 to female luer-type connector 1b, needle 10 may not be centered with respect to through hole 5, thereby exposing an edge of needle 10 to the fluid path as illustrated in FIG. 4. Although drilling through hole 5 to have a smaller diameter could potentially eliminate exposure of the needle edge to through hole 5, decreasing the diameter of through hole 5 will create a flow restriction.

In the devices and systems of the present invention, proximal end 210 of needle 200 (for example, formed from a metal such as stainless steel) is flared to create a larger opening at the entrance of needle 200 (see, for example, FIG. 2A). This flare moves the perimeter of edge of needle 200 further away from the outer edge of through hole 352 of second cooperating connector 348. Even in the case of misalignment (for example, resulting from required assembly tolerances or the hole tolerances themselves) the perimeter of edge of proximal end 210 of needle 200 will not be exposed to the fluid path. In the present invention, [[the]] at least a portion of the outer diameter or OD of needle 200 downstream (that is toward the needle tip or distal end) from flared proximal end 210 was effectively enlarged to the same diameter or a greater diameter than the outer perimeter of the flare by sliding a bushing or sleeve 220 (for example, formed from a material such as stainless steel) over distal end 230 of needle 200 until it contacted flare end 210. The outer diameter of sleeve 200 can, for example, be dimensioned appropriately for (for example, slightly smaller than) the diameter of mounting hole 354 in second cooperating connector 340, while the inner diameter is dimensioned appropriately for proper mounting to needle 200. The length of sleeve 220 can, for example, be at least as long as required to engage the entire length of mounting hole 354. Sleeve 220 can, for example, be attached by adhering, welding or soldering to needle 200. The resultant needle assembly is then inserted into second cooperating connector (as, for example, illustrated in FIG. 2A), forcing the flare against the flange located at the base of mounting hole 354 to effect a seal. In several embodiments, wherein second cooperating connector was formed from a metal such as stainless steel, second cooperating connector 340 was then, for example, soldered or welded to sleeve 220. The design of the present invention eliminates both any potential mismatch between needle 200 and through hole 352 and any potential flow restriction of the typical needle (or other flow path element) connection.

In several representative embodiments of the present invention, needle 200 was flared at an included angle of 20° to a maximum diameter range of 0.038-0.041 inches. This flaring enlarged the opening of needle 200 to 0.025 inches from its 0.020 inch nominal inner diameter. The outer diameter of mounting sleeve 220 was 0.042 inches to approximately match the maximum flare diameter of 0.041 inches. Mounting sleeve 220 also functioned to stiffen needle 200 and was fabricated to run nearly the entire length of needle 200 in several embodiments. Mounting hole 354 in second cooperating connector 340 had a maximum diametric clearance of 0.0020 inches between the outer diameter of sleeve 220 to accommodate the soldering operation. A 0.020 inch±0.001 diameter hole provided an opening from second cooperating connector 340 into needle 200. With a maximum assembly tolerance set at 0.002 inches and a through hole tolerance set at 0.001 inches, the total "misalignment" between the opening of needle 200 and through hole 352 could be 0.003 inches. Flaring needle 200 thus provided a margin of 0.005 inches over the nominal diameter, thereby guaranteeing the needle edge stayed away from the lip of through hole 352.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A system for connecting a length of conduit to a fluid path element, comprising:
    a compressible sealing element positioned on a distal end of the length of conduit;
    a first cooperating connector positioned around the length of conduit proximal to the sealing element and comprising a first cooperating connection mechanism; and
    a second cooperating connector comprising a second cooperating connection mechanism and defining an inner surface and a passage therein in fluid connection with the fluid path element, the first cooperating connection mechanism and the second cooperating connection mechanism each being adapted to form a connection between the first cooperating connector and the second cooperating connector, the connection causing compression of the sealing element;
    wherein a distal end of the sealing element and the inner surface of the second cooperating connector are tapered to approximately the same angle to create a seal between the inner surface of the second cooperating connector and the distal end of the sealing element;
    wherein the fluid path element is an injection needle comprising a lumen therethrough and having a length, a diameter of the lumen being flared outward to a larger diameter at a proximal end of the injection needle, an inner diameter of the proximal end of the injection needle being greater than a diameter of the passage of the second cooperating connector, an outer diameter of the proximal end of the injection needle also being flared outward; and
    further wherein the second cooperating connector further defines a mounting hole in fluid connection with the passage, the mounting hole having a diameter larger than the outer diameter of the proximal end of the injection needle, the system further comprising a sleeve positioned around and contacting substantially the entire length of the injection needle and having an outer diameter at least equal to the outer diameter of the flared proximal end of the injection needle and less than the diameter of the mounting hole, a proximal end of the sleeve abutting the injection needle along the flared proximal end thereof, the sleeve and at least the proximal end of the injection needle being received within the mounting hole.

2. The system of claim 1 wherein at least one of the first cooperating connection mechanism and the second cooperating connection mechanism comprises threading.

3. The system of claim 1 wherein the first cooperating connector is a male luer-type connector comprising threading and the second cooperating connector is a female luer-type connector.

4. The system of claim 1 wherein the sleeve extends over the majority of the length of the injection needle.

5. The system of claim 1 wherein the sealing element comprises an elastomeric material.

6. The system of claim 1 wherein the sealing element is formed integrally and of the same material as the conduit.

7. The system of claim 1 wherein the distal end of the sealing element is flush with the distal end of the length of conduit.

8. The system of claim 1 wherein the first cooperating connector further comprises a distal end surface that is adapted to contact a proximal end shoulder of the sealing element to compress the sealing element when the first cooperating connector and the second cooperating connector are connected.

9. A system for connecting to a fluid path section, comprising:
    a connector comprising a connection mechanism to connect the connector to the fluid path section, wherein the connection mechanism defines a passage therethrough in fluid connection with a mounting hole defining a surface;
    an injection needle disposed at least partially in the mounting hole and in fluid connection with the passage downstream of the connector, the injection needle comprising a lumen therethrough and having a length, a diameter of the lumen being flared outward to a larger diameter at a proximal end of the injection needle, the proximal end of the injection needle abutting the surface of the mounting hole of the connector, an inner diameter of the proximal end of the injection needle being greater than a diameter of the passage of the connector, an outer diameter of the proximal end of the injection needle also being flared outward; and
    a sleeve positioned around and contacting substantially the entire length of the injection needle, the sleeve having an outer diameter at least equal to the outer diameter of the proximal end of the injection needle, a proximal end of the sleeve abutting the injection needle along the flared proximal end thereof, the sleeve being at least partially received within the mounting hole.

10. The system of claim 9 wherein the sleeve extends over the majority of the length of the injection needle.

11. The system of claim 9 wherein the connector is a second cooperating connector and the fluid path section comprises a first cooperating connector to which the second cooperating connector is connectable.

12. The system of claim 11 wherein at least one of the first cooperating connector and the second cooperating connector comprises threading.

13. The system of claim 12 wherein the first cooperating connector is a male luer-type connector comprising threading and the second cooperating connector is a female luer-type connector.

14. The system of claim 12 wherein the fluid path section further comprises a length of conduit comprising a compressible sealing element positioned on a distal end of the length of conduit, the first cooperating connector being positioned around the length of conduit proximal to the sealing element, and further wherein a connection between the first cooperating connector and the second cooperating connector causes compression of the sealing element.

15. The system of claim 14 wherein a distal end of the sealing element is shaped to approximately conform to an inner surface of the second cooperating connector with which the distal end of the sealing element comes into contact.

16. The system of claim 15 wherein each of the distal end of the sealing element and an inner surface of the second cooperating connector are tapered to approximately the same angle to create a seal between the inner surface of the second cooperating connector and the distal end of the sealing element.

17. The system of claim 14 wherein the sealing element comprises an elastomeric material.

18. A system for connecting a length of conduit to a fluid path element, comprising:

a compressible sealing element positioned on a distal end of the length of conduit;

a first cooperating connector positioned around the length of conduit proximal to the sealing element and comprising a first cooperating connection mechanism;

a second cooperating connector comprising a second cooperating connection mechanism and defining an inner surface and a passage therein in fluid connection with a mounting hole, the first cooperating connection mechanism and the second cooperating connection mechanism each being adapted to form a connection between the first cooperating connector and the second cooperating connector, the connection causing compression of the sealing element;

wherein a distal end of the sealing element and the inner surface of the second cooperating connector are tapered to approximately the same angle to create a seal between the inner surface of the second cooperating connector and the distal end of the sealing element;

wherein the fluid path element is an injection needle comprising a lumen therethrough and having a length, a diameter of the lumen being flared outward to a larger diameter at a proximal end of the injection needle, an inner diameter of the proximal end of the injection needle being greater than a diameter of the passage of the second cooperating connector, an outer diameter of the proximal end of the injection needle also being flared outward; and a sleeve positioned around and contacting substantially an entire length of the injection needle and having an outer diameter at least equal to the outer diameter of the flared proximal end of the injection needle and less than a diameter of the mounting hole, a proximal end of the sleeve abutting the injection needle along the flared proximal end thereof, the sleeve and at least the proximal end of the injection needle being received within the mounting hole.

* * * * *